United States Patent [19]

Pavan et al.

[11] 4,111,993
[45] Sep. 5, 1978

[54] PROCESS FOR RACEMIZATION OF ALLETHROLONE

[75] Inventors: Charles Pavan, Nogent-sur-Marne; Jacques Bulidon, Paris, both of France

[73] Assignee: Roussel Uclaf, Paris, France

[21] Appl. No.: 795,021

[22] Filed: May 9, 1977

[30] Foreign Application Priority Data

May 14, 1976 [FR] France ............................... 76 14617

[51] Int. Cl.$^2$ ..................... C07C 45/00; C07C 45/24; C07C 49/46; C07B 20/00
[52] U.S. Cl. ................................. 260/586 R; 560/231
[58] Field of Search ..................... 260/586 R; 560/231

[56] References Cited

U.S. PATENT DOCUMENTS 3,981,919  9/1976  Umemura et al. ............... 260/586 R
4,001,334  1/1977  Umemura ........................ 260/586 R

OTHER PUBLICATIONS

La Forge et al., "J.A.C.S.", vol. 74, p. 5392 (1954).

Primary Examiner—Norman Morgenstern
Attorney, Agent, or Firm—Hammond & Littell

[57] ABSTRACT

A novel process for the preparation of racemic allethrolone of the (R,S) configuration comprising heating optically active allethrolone of the (R) configuration or of the (S) configuration or a mixture of the (R) and (S) configurations in non-equimolecular proportions with formic acid to form the formate of racemic allethrolone of (R,S) configuration and hydrolyzing the latter in the presence of an acid or base to obtain racemic (R,S) allethrolone.

9 Claims, No Drawings

PROCESS FOR RACEMIZATION OF ALLETHROLONE

STATE OF THE ART

It is known that optically active allethrolone of (S) configuration leads, in general, by esterification with cyclopropane carboxylic acids to esters having a clearly superior insecticidal activity than the esters of the same acids with optically active allethrolone of the (R) configuration or racemic (R,S) allethrolone. Optically active allethrolone of (S) configuration may be obtained by resolution processes such as described in French Pat. No. 2,166,503 which apart from (S) allethrolone leaves (R) allethrolone or a mixture of (R) and (S) allethrolone rich in (R) allethrolone. It is clearly seen that it is highly desirable to provide a process for the transformation of (R) allethrolone or mixtures of (R) and (S) allethrolone rich in (R) allethrolone into (S) allethrolone whose cyclopropane-carboxylic acid esters possess a greater insecticidal activity.

OBJECTS OF THE INVENTION

It is an object of the invention to provide a process for the preparation of racemic (R,S) allethrolone from (R) or (S) allethrolone or mixtures of (R) and (S) allethrolone in non-equimolecular proportions.

This and other objects and advantages of the invention will become obvious from the following detailed description.

THE INVENTION

The novel process of the invention for the preparation of racemic (R,S) allethrolone comprises heating optically active allethrolone of the (R) configuration or of the (S) configuration or a mixture of the (R) and (S) configurations in non-equimolecular proportions with formic acid to form the formate of racemic allethrolone of (R,S) configuration and hydrolyzing the latter in the presence of an acid or base to obtain racemic (R,S) allethrolone. In a preferred mode of the process, the heating is effected at the reflux temperature of the mixture but temperatures near the reflux temperature are equally useful.

The acid agent present for the hydrolysis of the formate of racemic allethrolone is preferably a strong acid used in a dilute solution such as hydrochloric acid and especially sulfuric acid. Preferably, the hydrolysis of the formate of racemic allethrolone is effected by heating in an about 1N aqueous solution of sulfuric acid.

The hydrolysis of the formate of racemic allethrolone may also be effected in the presence of a basic agent which should be sufficiently basic to permit saponification of the formate of allethrolone. When the base used is a strong base, a quantity greater than the stoichiometric amount should not be used to avoid alteration of the liberated allethrolone. The basic agent used to effect the hydrolysis is preferably sodium hydroxide or potassium hydroxide used in stoichiometric amounts.

A preferred mode of the process of the invention to produce racemic (R,S) allethrolone comprises refluxing a mixture of formic acid with (R) or (S) allethrolone or with a mixture of (R) and (S) allethrolone in non equimolecular proportions to form the formate of (R,S) allethrolone and hydrolyzing the latter by heating in an about 1N aqueous sulfuric acid solution.

The process of the invention permits the transformation of (R) allethrolone or a mixture of (R) and (S) allethrolone rich in (R) allethrolone into racemic (R,S) allethrolone under conditions easily attainable on an industrial scale. Thus, it is possible to resolve the racemic allethrolone to recover the desired (S) allethrolone formed at the expense of the (R) allethrolone, and thus, to revalorize this enantiomer.

The invention also comprises a process as hereinbefore defined in which the starting material is (R) allethrolone or a mixture of (R) and (S) allethrolone rich in (R) allethrolone.

The process of the invention has the unexpected character in that there exists few exemples of racemization in an acid media of allylic alcohols of the aliphatic series and the racemization of allethrolone which presents a great industrial importance has until now not been realized with success. Allethrolone is very special cyclic allylic alcohol given the presence of 2,3-double bond in the ring which is conjugated with a ketone function and the existence of the ketone function which activates the hydrogen α to the alcohol function. This particular structure of allethrolone makes it fragile in acid media and would lead one skilled in the art to fear that the racemization attempts by heating allethrolone in an acid media would lead to undesired side reaction.

The heating of allethrolone in acid media leads to the expectation that the symetric, intermediate carbocation necessary for the racemization

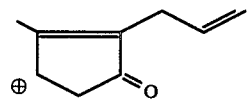

A would, by the grace of the activation of the hydrogen α to the carbon carrying the ⊕ charge, by the ketone group, lead to the formation of a dienic compound

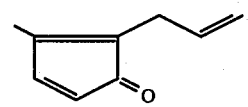

B itself very reactive and susceptible to change into a compound of the dimer type, rather than the desired racemization. It has been established in a surprising manner that the choice of formic acid permits in a large measure to avoid the annoying secondary reaction.

The final hydrolysis of formate of allethrolone in acid media can also give rise to analogous risks. The use of dilute aqueous solutions of strong acids permits the avoiding of any inconvenience.

The hydrolysis of the formate of allethrolone in strong basic media equally would lead to parasite reactions such as described by Laforge [J.A.C.S., Vol. 74 (1952), p. 5392] notably the formation of compounds of the type

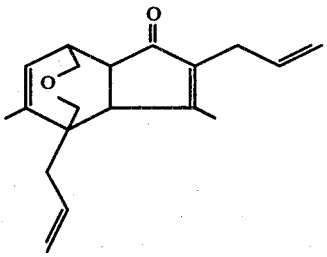

The utilization in the preferred mode of the process of the invention of a quantity of a strong base which is not greater than the stoichometric amount permits the avoidance of such parasitic reactions.

In summary, in spite of the fragility of the allethrolone molecule in acid media as well as in basic media which would give rise, a priori to the expectation of the existence of very annoying secondary reactions, it has suprisingly been discovered that the process of the invention leads to the desired racemization with satisfactory yields.

In the following examples there are described several preferred embodiments to illustrate the invention. However, it should be understood that the invention is not intended to be limited to the specific embodiments.

EXAMPLE 1

Racemization of (R) allethrolone

STEP A: Formate of racemic allethrolone 50 g of (R) allethrolone were added under an inert atmosphere to 250 ml of 98% formic acid containing 0.75% water and the mixture was heated to reflux in about 30 minutes and reflux was maintained for 24 hours. The mixture was cooled to 20° C and was then poured into water. The mixture was extracted with methylene chloride and the organic extracts were neutralized with aqueous sodium bicarbonate. The aqueous phase was saturated with sodium chloride. The methylene chloride phase was washed with an aqueous solution saturated with sodium chloride, was dried and concentrated to dryness under reduced pressure to obtain 64 g of raw formate of racemic allethrolone with a specific rotation $[\alpha]_D^{20} = 0°$ (c = 10% in chloroform). Saponification index = 370 mg. KOH/g (theoretical - 311) and acid index = 2.5 mg KOH/g (theoretical — 0).

STEP B: Racemic (R,S) allethrolone 64 g of the product of Step A were added at 85° C under nitrogen to 256 ml of aqueous N sulfuric acid and the mixture was heated to reflux over 30 minutes. Reflux was maintained for 3 hours and the mixture was then cooled to 0° C. The mixture was neutralized with sodium hydroxide solution and was then saturated with sodium chloride. The aqueous phase was extracted with methylene chloride and the organic phase was dried, decolorized with activated carbon and concentrated to dryness under reduced pressure. The residue was rectified under reduced pressure to obtain 23.1 g of racemic (R,S) allethrolone with a specific rotation $[\alpha]_D^{20} = 0°$ C (c = 10% in chloroform). Acid index = 1 mg of KOH/g and the hydroxyl index was 96%.

EXAMPLE 2

38 kg of a mixture of 60% (R) allethrolone and 40% of (S) allethrolone resulting from the industrial resolution of racemic allethrolone and having a specific rotation $[\alpha]_D^{20} = -7.5°$ C (c = 10% in chloroform) and the proportion of which is shown by its circular dichroism, were added to 190 liters of formic acid and the mixture refluxed with stirring under nitrogen at a temperature of about 102° C for 26 hours. The mixture was cooled and residual formic acid was distilled under reduced pressure to obtain raw formate of racemic (R,S) allethrolone which was used as is for the next step.

A mixture of 1.24 liters of sulfuric acid (d = 1.838) and 89 liters of water were added to the product above and the mixture was heated at 50° C with stirring for 2 hours and was then cooled. The pH of the mixture was adjusted to 7 with aqueous 10N sodium hydroxide solution (about 36 liters) and the mixture was stirred while adding 42 kg of sodium chloride. The aqueous phase of the mixture was extracted with methylene chloride and the combined organic extracts were dried, treated with activated carbon, stirred and filtered. The filtrate was evaporated to dryness under normal pressure and the 35.5 kg of residue was rectified under reduced pressure to obtain 29.15 Kg of racemic (R,S) allethrolone with a boiling point of 125° C at 1 mm Hg and a specific rotation $[\alpha]_D^{20} = -1°$ C (c = 10% in chloroform) UV absorption: $E_{1cm}^1 = 780$ at 230 nm.

Various modifications of the process of the invention may be made without departing from the spirit or scope thereof and it should be understood that the invention is intended to be limited only as defined in the appended claims.

WE CLAIM:

1. A process for the preparation of racemic (R,S) allethrolone comprising heating optically active allethrolone of the (R) configuration or of the (S) configuration or a mixture of the (R) and (S) configurations in non-equimolecular proportions with formic acid to form the formate of racemic allethrolone of (R,S) configuration and hydrolyzing the latter in the presence of an strong acid or strong base to obtain racemic (R,S) allethrolone.

2. The process of claim 1 wherein the heating with formic acid is effected at the reflux temperature of the mixture.

3. The process of claim 1 wherein the hydrolysis is effected with a dilute solution of a strong acid.

4. The process of claim 3 wherein the acid is sulfuric acid.

5. The process of claim 4 wherein the acid is about N sulfuric acid.

6. The process of claim 1 wherein the hydrolysis is effected in the presence of about a stoichiometric amount of a basic agent.

7. The process of claim 6 wherein the basic agent is selected from the group consisting of potassium hydroxide and sodium hydroxide.

8. The process of claim 1 wherein the starting allethrolone is (R) allethrolone.

9. The process of claim 1 wherein the starting allethrolone is a mixture of (R) and (S) allethrolone rich in (R) allethrolone.